United States Patent [19]
Klaas

[11] Patent Number: 5,741,244
[45] Date of Patent: Apr. 21, 1998

[54] PROBE FOR THE SUCTIONING OF OCULAR TISSUE

[76] Inventor: Dieter Klaas, Bahnhofstrasse 5, D-86316 Friedberg, Germany

[21] Appl. No.: 402,177

[22] Filed: Mar. 13, 1995

[51] Int. Cl.[6] ................................................ A61B 17/36
[52] U.S. Cl. .................................................. 606/4; 606/15
[58] Field of Search ............................... 606/4, 5, 6, 14, 606/15, 16, 17

[56] References Cited

U.S. PATENT DOCUMENTS

| | | | |
|---|---|---|---|
| 4,694,828 | 9/1987 | Eichenbaum | 606/6 |
| 4,825,865 | 5/1989 | Zelman | 606/6 |
| 5,163,935 | 11/1992 | Black et al. | 606/17 |
| 5,224,942 | 7/1993 | Beuchat et al. | 606/15 |
| 5,257,988 | 11/1993 | L'Esperance, Jr. | 606/6 |
| 5,324,282 | 6/1994 | Dodick | 606/15 |
| 5,370,649 | 12/1994 | Gardetto et al. | 606/17 |
| 5,377,683 | 1/1995 | Barken | 606/15 |
| 5,445,637 | 8/1995 | Bretton | 606/6 |

*Primary Examiner*—Jennifer Bahr
*Assistant Examiner*—Sonya Harris-Ogugua
*Attorney, Agent, or Firm*—Evenson, McKeown, Edwards & Lenahan, PLLC

[57] ABSTRACT

A probe for suctioning of ocular tissue includes a hollow suction needle having a lateral opening in a needle region to be placed on the ocular tissue to be suctioned, a laser radiation source, a hollow mirror surface defining an ellipsoidal cavity within the needle region and forming a reflective device with a first focal point within the cavity and a second focal point outside of the cavity for location in the tissue to be suctioned, and a light guide disposed within and extending through the suction needle and interconnecting the laser radiation source and the ellipsoidal cavity. The laser radiation is directed by the light guide to the first focal point and reflected by the hollow mirror surface to the second focal point.

8 Claims, 2 Drawing Sheets

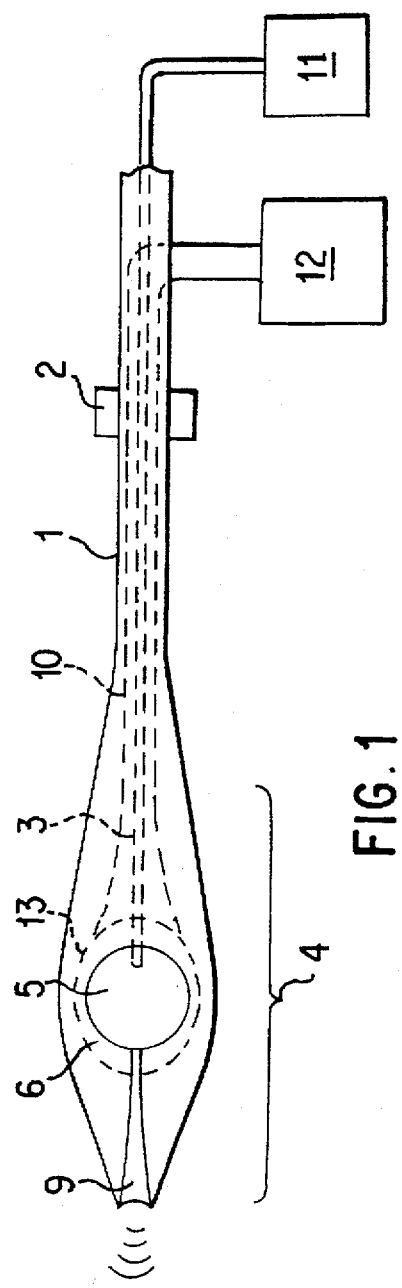
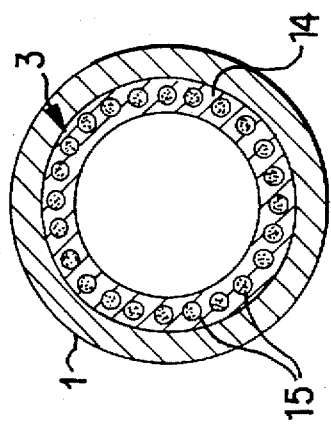
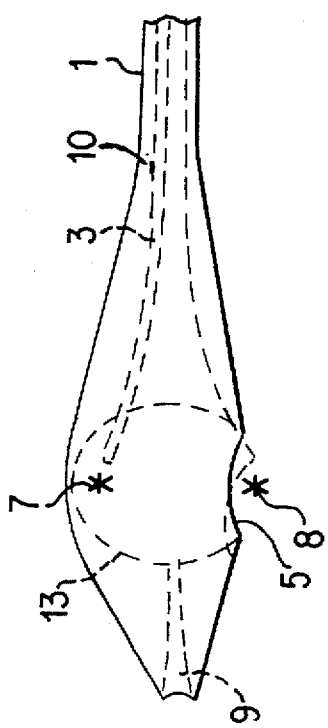

PROBE FOR THE SUCTIONING OF OCULAR TISSUE

FIELD OF THE INVENTION

This invention pertains to a probe for suctioning of ocular tissue.

BACKGROUND OF THE INVENTION

A probe of this type is known from German patent publication 4,038,773 C2. For the known probe, laser radiation, in particular, pulsed laser radiation is brought to the vicinity of the tip of the suction needle, so that the ocular tissue to be suctioned is broken up to an increased degree and can be more easily suctioned. For the known probe, the suction needle is moreover connected to an ultrasonic source in order for the needle section inserted in the tissue to achieve a disintegration and emulsification of the ocular tissue in order to facilitate the suctioning.

SUMMARY OF THE INVENTION

The purpose of the invention is to achieve an improved disintegration and emulsification of the tissue in order to facilitate suctioning.

This problem is solved according to the invention.

For the invention, the needle region which is capable of being placed on the ocular tissue to be suctioned is provided with a lateral opening through which the laser radiation is emitted onto the tissue. The opening simultaneously serves to draw off the disintegrated and/or emulsified tissue.

The laser radiation is guided by means of a light guide into a cavity in the vicinity of the lateral opening and there, by means of reflection off the wall of the cavity, is radiated through the lateral opening onto the tissue. The laser radiation can still be focused at this time. For this purpose, the inner wall of the cavity in the suction needle can be configured as a concave mirror. The concave mirror surface preferably possesses the shape of an ellipsoid. The laser radiation is guided to a focal point of the ellipsoid and is directed to the other focal point by means of reflection. This [second] focal point preferably lies in the tissue to be disintegrated. The laser radiation generates a plasma that emulsifies the ocular lens tissue.

The laser radiation guide can be moved into the one focal point of the ellipsoid and again be removed from the focal point, so that, if needed, laser radiation can be radiated onto the tissue to be suctioned.

In order to intensify the disintegration effect, the hollow suction needle is also connected to an ultrasonic source. In particular, the needle tip has a section of a funnel shaped configuration that causes an amplified sound radiation in the tissue to be disintegrated. This radiation funnel for ultrasonic waves can, however, also be directed laterally on the side of the opening for laser radiation.

The ellipsoidal cavity configuration in the needle interior has an additional disintegrating effect during the suctioning of the ocular tissue, since the suctioned pieces of tissue, upon impact with the inner wall, are additionally disintegrated and can be more easily suctioned.

The pulsed laser radiation additionally causes the formation of cavitation and pressure waves in the cavity of the focusing device and suction tube. This also increases the disintegrating action on the tissue to be suctioned.

The probe is preferably employed as a phaco-probe for the suctioning of natural ocular lens tissue, e.g., for a cataract operation.

BRIEF DESCRIPTION OF THE INVENTION

The invention is explained in more detail using an embodiment, with the aid of the figures.

Shown are:

FIG. 1 a side view of an embodiment of a phaco-probe;

FIG. 2 a top view of the embodiment of FIG. 1; and

FIG. 3 a cross section through the suction channel of a further embodiment; and

FIG. 4 a side sectional view of another embodiment.

DETAILED DESCRIPTION OF THE INVENTION

Figure 4:
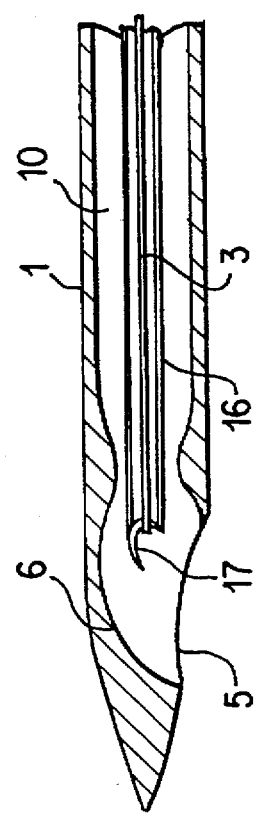

The phaco-probe represented possesses a suction needle (1). A suction channel (10), to which is connected a vacuum pump (12) (aspirator) extends within the suction needle. The suction needle is also connected to an ultrasonic source (2). The suction needle (1) possesses a needle region (4) that is brought into the vicinity of the tissue to be suctioned. In the case of a cataract operation, this region is introduced, through a section at the lateral edge of the eye to be operated upon, into the anterior chamber of the eye.

The needle region (4) possesses a lateral opening (5). This lateral opening (5) forms an opening for an ellipsoidal interior space (13) in the interior of the needle. The suction channel (10) opens into the ellipsoidal cavity (13).

The ellipsoidal cavity (13) also forms a focusing device (6) for a laser beam, that is moved onto an internal focal point (7) of the ellipsoidal cavity with the help of a light guide device (3) or other radiation guiding device. The light guide device (3) configured, e.g., as a glass fiber bundle is connected to a laser radiation source (11). Flashes of laser radiation in the region of the focal point (7) are reflected by the ellipsoidal reflecting concave mirror surface of the interior space (13) and are, in the main, directed to an exterior focal point (8). This focal point (8) lies in the region of the tissue to be suctioned, preferably outside the lateral opening (5) as can be seen from FIG. 2.

The arrangement of the forward fiber tip, for releasing laser flashes, of the light guide device (3), preferably guided to be movable in the suction needle (1), can be such that a focusing of the reflected laser radiation, which is discharged in all directions from the tips of the glass fibers in the region of the focal point (8) lying outside of the opening (5), takes place.

While for the embodiment of FIG. 1, the light guide device (3) is configured as a glass fiber bundle, primarily running parallel to the axis of the suction channel (10), the light guide device (3) for the embodiment of FIG. 3 is formed by means of several light guides (15), in particular, in the form of several glass fiber bundles uniformly distributed around the perimeter of the suction channel (10). Here, the light guides (15) are embedded in an inner wall coating (14). The wall of the suction needle (1) can consist of titanium or ceramic. An inner coating capable of conducting laser radiation is used in the suction needle (1) for the embodiment of FIG. 3. The laser radiation guided in the light guides (15) is directed in the vicinity of the inner focal point (7) or on this focal point such that a focusing of the laser radiation is achieved in the region of the outer focal point (8).

Another reflecting surface can also be employed as the concave mirror surface, in which a focusing of the laser radiation reflected by the wall of the cavity (13) takes place by means of a corresponding arrangement of the glass fiber tip or tips, somewhat outside the lateral opening (5).

The invention makes it possible to treat, with laser radiation, specific regions of the ocular tissue to be suctioned, in which other regions of the eye, in particular, ocular regions sensitive to laser radiation, e.g., the retina, are included. This achieves a targeted treatment of the tissue regions to be suctioned by means of laser radiation.

The opening (5) can run parallel to the needle axis. It can also, however, have a diagonal curve, as is clear from the dashed line in FIG. 2.

The suction needle (1) is also connected to the ultrasonic source (2). Radiation of the ultrasonic waves occurs in the needle region (4). A funnel shaped needle section (9) is preferably used, which causes an amplification of the radiated sound waves. The funnel can be provided, as the embodiment shows, at the tip of the needle region (4). It can also, however, open laterally, on the side at which the opening (5) is located.

Ocular tissue to be removed is sucked through the lateral opening (5), under the effect of the vacuum pump (12), into the cavity (13). From there it reaches the suction channel (10).

In the embodiment of FIG. 4, an ultrasonic waveguide (16) is located in the suction channel (10) of the suction needle (1). This ultrasonic waveguide (16) is connected to an ultrasonic source, not represented here, that can be configured as the ultrasonic source (2) shown in FIG. 1. The ultrasonic waveguide (16) is of a hollow configuration and extends along the axis of the hollow suction needle (1).

The light guide device (3), connected to a laser radiation source not represented here is located in the interior of the hollow ultrasonic waveguide (16). The laser radiation source can be configured the same as the laser radiation source (11) in FIG. 1.

The anterior end of the ultrasonic waveguide (16), configured as the sound radiating end (17), projects into the cavity of the focusing device (6). The radiation releasing end of the light guide device (3) also projects into the cavity of the focusing device (6). The focusing device (6) can have the shape of an ellipsoid. Both the ultrasonic waveguide (16) as well as the light guide device (3) can be moved in the axial direction, such that their front ends, releasing ultrasonic waves or laser radiation respectively, can be arranged within the focusing device (6) at the focal point or at such locations at which the disintegration of the tissue to be suctioned is achieved with the greatest efficiency.

The ultrasound radiating end (17) of the ultrasonic waveguide (16) can be of a concave configuration as is represented in FIG. 4. The front end of the light guide device (3) releasing laser radiation projects into this concave cavity.

The disintegrated tissue is suctioned through the suction channel (10), which is connected to a vacuum pump (12) represented by way of example in FIG. 1.

Ocular tissue suctioned moves along the ultrasonic waveguide (16) through the suction channel (10). This further disintegrates the tissue through the effect of the ultrasonic oscillations of the ultrasonic waveguide (16).

I claim:

1. A probe for suctioning of ocular tissue comprising:

a hollow suction needle having a lateral opening in a needle region capable of being placed on the ocular tissue to be suctioned;

a laser radiation source for generating laser radiation;

a hollow mirror surface defining an ellipsoidal cavity within said needle region and forming a reflective device with a first focal point within said cavity and a second focal point outside of said cavity for location in the tissue to be suctioned; and a light guide device disposed within and extending through said suction needle and interconnecting the laser radiation source and the ellipsoidal cavity;

said laser radiation being directed by the light guide device to said first focal point and reflected by the hollow mirror surface to said second focal point.

2. A probe as defined in claim 1, and further comprising an ultrasonic source to which the suction needle is connected and wherein the needle region capable of being placed on the ocular tissue to be suctioned radiates ultrasonic waves.

3. A probe as defined in claim 2, wherein the needle region capable of being placed on the ocular tissue to be suctioned includes a section of a funnel shaped configuration for radiating sound.

4. A probe as defined in claim 3, wherein the funnel shaped section is located between the ellipsoidal cavity and a tip of the needle.

5. A probe as defined in claim 1, wherein the light guide device includes light guides distributed over an entire perimeter of an inner wall of a suction channel in said hollow suction needle.

6. A probe as defined in claim 1, wherein the light guide device includes one light guide running parallel to an axis of a suction channel in said hollow suction needle.

7. A probe as defined in claim 1, and further comprising an ultrasonic waveguide guided through a suction channel in the hollow suction needle and having a sound-radiating end which projects into the ellipsoidal cavity.

8. A probe as defined in claim 7, wherein the light guide device is located in the ultrasonic waveguide.

* * * * *